United States Patent
Bille

[19]

[11] Patent Number: 5,822,035
[45] Date of Patent: Oct. 13, 1998

[54] ELLIPSOMETER

[75] Inventor: Josef F. Bille, Heidelberg, Germany

[73] Assignee: Heidelberg Engineering Optische Messysteme GmbH, Germany

[21] Appl. No.: 709,243

[22] Filed: Aug. 30, 1996

[51] Int. Cl.[6] .................................................. A61B 3/10
[52] U.S. Cl. ......................................... 351/215; 351/246
[58] Field of Search .................................. 351/205, 206, 351/215, 221, 211, 212, 246, 247

[56] References Cited

U.S. PATENT DOCUMENTS

| | | |
|---|---|---|
| 4,053,845 | 10/1977 | Gould . |
| 4,069,823 | 1/1978 | Isakov et al. . |
| 4,091,274 | 5/1978 | Angelbeck et al. . |
| 4,091,814 | 5/1978 | Togo . |
| 4,503,854 | 3/1985 | Jako . |
| 4,517,980 | 5/1985 | Tagnon . |
| 4,579,430 | 4/1986 | Bille . |
| 4,601,288 | 7/1986 | Myers . |
| 4,665,913 | 5/1987 | L'Esperance, Jr. . |
| 4,669,466 | 6/1987 | L'Esperance . |
| 4,771,542 | 9/1988 | Ichihashi et al. . |
| 4,772,115 | 9/1988 | Gersten et al . |
| 4,773,414 | 9/1988 | L'Esperance, Jr. . |
| 5,062,702 | 11/1991 | Bille . |
| 5,246,435 | 9/1993 | Bille et al. . |
| 5,303,709 | 4/1994 | Dreher et al. . |

OTHER PUBLICATIONS

G. Walsh et al, *Objective Technique for the Determination of Monochromatic Aberrations of the Human Eye*, pp. 987–992, Journal of Optical Society of America, vol. 1, No. 9, Sep. 1984.

Krauss et al., *Laser Interactions with the Cornea,* pp. 37–52, Survey of Ophthalmology, vol. 31, No. 1, Jul.–Aug. 1986.

Klyce et al., *Imaging, Reconstruction, and Display of Corneal Topography*, pp. 409–416, SPIE, vol. 1161, 1989.

Bille et al., *Imaging of the Retina by Scanning Laser Tomography*, pp. 417–425, SPIE, vol. 1161, 1989.

Phillip C. Baker, *Holographic Contour Analysis of the Cornea*, pp. 426–437, CPIE, vol 1161, 1989.

*Primary Examiner*—Hung X. Dang
*Attorney, Agent, or Firm*—Nydegger & Associates

[57] ABSTRACT

A system and method for the in-vivo measurement of optical characteristics of a cornea includes an ellipsometer which measures the phase shift in reflected light after it has passed through the cornea or been reflected from the retina. This ellipsometer has a polarizing unit which selectively irradiates the cornea with light having one of four preselected linearly independent states of polarization (irradiation states). For each irradiation state, an analyzing unit in the ellipsometer selectively detects reflected light with one of four preselected linearly independent states of polarization (detection states). With the consequent sixteen ellipsometer measurements, a Müller matrix is generated which reveals the birefringent characteristics of the portion of the cornea through which the light passed. These measurements are then used in determining the birefringent characteristics of the cornea. Alternatively, birefringent properties of the deeper retinal layers can be determined.

23 Claims, 3 Drawing Sheets

ELLIPSOMETER

FIELD OF THE INVENTION

The present invention pertains generally to optical diagnostic systems. More particularly, the present invention pertains to systems which measure the optical characteristics of biological samples. The present invention is particularly, but not exclusively useful as an ellipsometer for measuring the birefringent characteristics of the cornea and the retina of an eye.

BACKGROUND OF THE INVENTION

It is well known that various visual deficiencies and maladies can be surgically corrected by restructuring the cornea of an eye. Typically, this restructuring is done by making incisions into the cornea, or by removing portions of the corneal tissue. For example, myopia has been successfully corrected by operations such as radial keratotomy or excimerlaser photorefractive Keratectomy. Unfortunately, successful operations for some maladies such as astigmatism, have not always been possible. Indeed, the surgical correction of corneal astigmatism has been notoriously unpredictable. Several reasons can be given for this, the most important of which pertain to the refractive properties of the cornea.

In order to predict the effect a corneal incision will have on the refractive properties of the cornea, it is known that several factors should be considered. These include: 1) the thickness of the cornea, 2) the intraocular pressure, and 3) the stress distribution inside the cornea. Of these, the thickness of the cornea and the intraocular pressure are both rather easily measured. On the other hand, an in vivo preoperational measurement of the stress distribution in the cornea has not been possible. The consequence of this is that, without information about stress distribution in the cornea, only incomplete information has been available. Thus, whatever actual effect a corneal relaxation incision may have had on the refractive properties of the cornea has not been determinable.

With specific consideration for the stress distribution in the cornea, it is known that this stress distribution is interrelated with the birefringent properties of the cornea. Consequently, a measurement of the birefringent properties of the cornea can be used to determine the stress distribution in the cornea.

For the present invention, measurement of the birefringent properties of the cornea is done optically and relies on the fact that these birefringent properties change the state of polarization of light that passes through the cornea. It happens that the changes can be mathematically described using a Stokes vector notation and the so-called Müller matrix of the medium.

As used here, the Stokes vector (S) consists of four components. These are: I, M, C and S. Considered individually, I describes the total intensity of the light beam, while M, C and S respectively describe the intensities of its three linear independent polarization states. Included in these three independent polarization states are factors which relate to the electrical field vectors, $E_x$, $E_y$ and their phase shift $\Psi$. Specifically:

$$M = \sqrt{<E_x^2> - <E_y^2>}$$

-continued
$$C = 2\sqrt{<E_x^2><E_y^2>} \quad \cos(\phi)$$

$$S = 2\sqrt{<E_x^2><E_y^2>} \quad \sin(\phi)$$

The polarized part $I_p$ of the light beam is then given by:

$$I_P = \sqrt{M^2 + C^2 + S^2}$$

It is particularly important to recognize that a Stokes vector which mathematically describes the cornea includes information about phase shift, $\Psi$. This is because, as we shall see, the phase shift $\Psi$ is determinative of the birefringent properties of the cornea, and, as stated above, the birefringent properties are determinative of the desired information about the stress distribution in the cornea.

It happens that as light passes through a birefringent medium, the Stokes vector S of light that is irradiated into the medium is changed. Specifically, as the light passes through the medium, the Stokes vector S, which is descriptive of the light entering the medium will change according to a Müller matrix of the medium. Thus, the Stokes vector S' which can be used to describe light that has passed through a medium having a Müller matrix (M) is give by the expression:

$$S'=M * S$$

This Müller matrix M is a 4×4 rotation matrix whose tilting angle directly determines the phase shift $\Psi$ of the specimen.

For the environment in which the present invention is to be used, several independent factors contribute to the overall Muller matrix M. These factors include not only the cornea, but also the lens of the eye and the ellipsometer which is to be used. Further, depending on where measurements are to be taken with the ellipsometer, anatomical structures other than the cornea may need to be considered. Specifically, as more fully disclosed below for the present invention, ellipsometer measurements can be taken by focusing on either 1) lamellae within the cornea, 2) the anterior surface of the lens, 3) blood vessels overlying the surface of the retina, or 4) the retina. Where measurements are taken with light reflected from the retina or from blood vessels on the retina, it will be appreciated that the lens and the aqueous humor in the eye will also make a small but generally uniform contribution to the Müller matrix.

In more detail, the Müller matrix determines a rotation of the Stokesvector on the three dimensional Poincaré sphere, which is defined in a coordinate system with the axes given by the components M, C and S. The angle of rotation is identical with the angle of retardation caused by the birefringent object and the eigenvector of the Müller matrix is related to the three dimensional position of the fast axis of this object.

For a measurement of the human cornea several birefringent components having their own Müller matrices have to be considered. Indeed, always the complete system with the Müller matrix $M_{all}$ is measured including the effect of the cornea represented by $M_{co}$, and the influence of the ellipsometer which is taken into account by $M_{sc}$. Thus, the measured Stokesvector $S_{out}$ can be written as:

$$S_{out}=M_{all} S_{in}$$
$$=M_{sc}M^2_{co}M_{sc}S_{in}.$$

To calculate $M_{co}$ it is necessary to know the matrix $M_{sc}$.

$$M^2{}_{co}=M_{sc}{}^{-1}M_{all}M_{sc}{}^{-1}$$

The measurements are performed by focusing the light beam onto the surface of the lens using the principle of confocal detection to eliminate disturbing surface reflections.

In addition, another method to measure the corneal birefringence is evaluated using light which is specularly reflected on retinal blood vessels. At the areas where blood vessels are lying above the nerve fibers the measured matrix is also given by $M_{all}=M_{sc} \ M^2{}_{co} \ M_{sc}$, which allows the calculation of $M_{co}$ by equation (2) assuming that the influence of the lens and the vitreous is small enough to be neglected.

Based on the 4×4 nature of the Müller matrix M, the present invention recognizes that sixteen measurements are needed to evaluate the determinant. Once evaluated, as indicated above, the Müller matrix M yields information about the phase shift Ψ and, consequently, information about the birefringent characteristics of the medium which can be used for surgical planning.

In light of the above, it is an object of the present invention to provide a system for the in-vivo measurement of optical characteristics of a cornea which includes measurements of the birefringent properties of the cornea to determine the mechanical stress distribution of the cornea for use in the planning of refractive-surgical operations. Another object of the present invention is to provide a system for the in-vivo measurement of optical characteristics of a cornea which requires only extremely short measurement times. Still another object of the present invention is to provide a system for the in-vivo measurement of optical characteristics of a cornea which is relatively easy to use and comparatively cost effective.

SUMMARY OF THE PREFERRED EMBODIMENTS

In accordance with the present invention, an ellipsometer system for in-vivo measurement of optical characteristics of the cornea of an eye includes components which have the capability of making sixteen independent measurements for each single sampling point. These components include a processor-controlled polarizing unit which generates a laser light beam having a preselected polarization state, and a processor-controlled analyzing unit which receives reflected light using a preselected detection state. The system also includes a computer which uses the obtained signals to calculate optical characteristics of the cornea.

The polarizing, or polarizer, unit of the ellipsometer includes a laser diode for generating the laser light beam. The polarizing unit also includes two Pockels cells for establishing a polarization state for the generated light beam. By the concerted operation of these two Pockels cells, phase shifts can be selectively imparted by the polarizing unit to generate four different irradiation (polarization) states for the light beam. These irradiation (polarization) states are: (0,0);(λ/4,0);(0,λ/2); and (λ/14,λ/12). Additionally, the analyzing, or analyzer, unit of the ellipsometer includes two Pockels cells. In an operation similar to the action of the Pockels cells of the polarizing unit, the Pockels cells of the analyzing unit impart phase shifts to establish four different detection states for the reflected light beam. These detection states are: (0,0); (λ/4,0); (0,λ/2); and (λ/4,λ/2). Thus, for each irradiation (polarization) state there are four detection states. The result is that, with reflections from one sampling point, sixteen different intensity states can be distinguished.

A computer is used to analyze the sixteen different intensity states received from each single sampling point. More specifically, the obtained signals are used mathematically to create sixteen equations from which the sixteen coefficients of the Müller matrix (M) are calculated. As indicated above, the Stokes vector of the light received by the analyzing unit (S') is determined by its relationship with the Stokes vector generated by the polarizing unit (S) namely:

$$S'=M^* \ S$$

In the operation of the ellipsometer system of the present invention, the ellipsometer is focused onto a sampling point. An Irradiation (polarization) state is then selected for the polarizing unit and a laser light beam is generated. The reflection of this light beam is then detected by the analyzing unit according to a preselected detection state of the analyzing unit. A signal is thus obtained. Using the same irradiation state for the polarizing unit, but a different detection state for the analyzing unit, another signal is similarly obtained. This continues until four different signals have been obtained using one irradiation state and four different detection states. The polarizing unit is then changed to generate a laser light beam having a different irradiation state, and the process is repeated to obtain four more signals. When all sixteen signals have been obtained from a single sampling point the computer calculates the Müller matrix for the medium through which the laser light beam has passed. Several such measurements can be taken and, as is the case for the present invention, the measurements are compared to identify regions of birefringent inhomogeneity in the medium.

With specific regard to the eye, the ellipsometer system of the present invention is useful for several types of measurements. Of particular importance, one type of measurement concerns the cornea, another concerns the lens, and yet another concerns the retina. In each case, the operation of the ellipsometer system is essentially the same with only the focal point being changed. For the cornea, the light beam can be focused on the anterior surface of the lens. For either the cornea or the lens, the light beam can be focused on a blood vessel overlying the retina. For the retina, the laser light beam is focused directly onto the neuronal retina.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
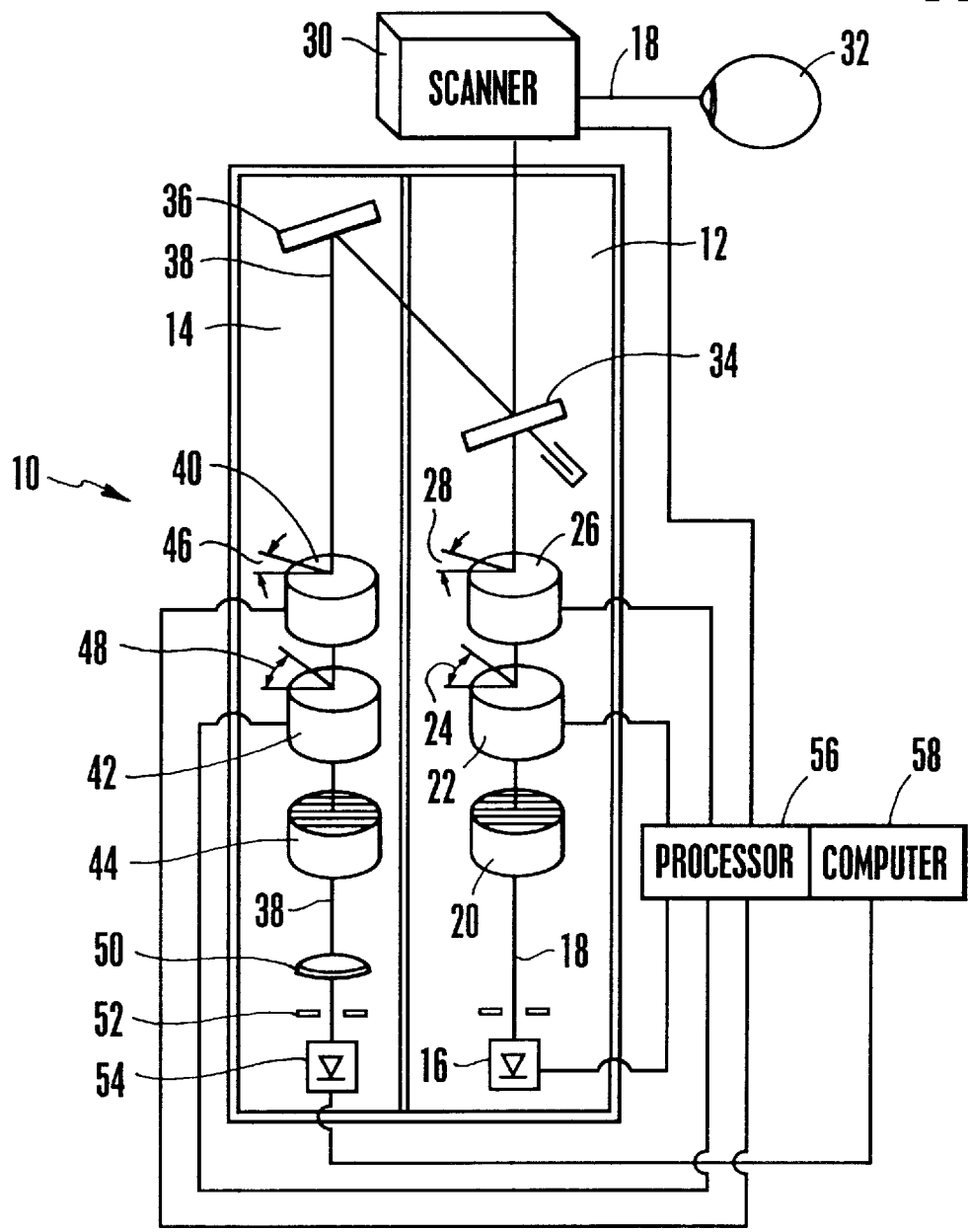
FIG. 1 is a schematic diagram of the ellipsometer of the present invention.

Referring initially to FIG. 1, an ellipsometer according to the present invention is shown and is generally designated 10. As shown, the ellipsometer 10 includes both a polarizing unit 12 and an analyzing unit 14. To begin with a consideration of the polarizing unit 12, it will be seen that the unit 12 includes a source of laser light, such as the laser diode 16. For the present invention, laser diode 16 can be of any type that is well known in the pertinent art and, preferably, the laser diode 16 emits a laser light beam having a wavelength of 785 nm.

Within the polarizing unit 12, the laser light beam that is emitted from laser diode 16 is directed along a path 18 toward a polarizer 20. Importantly, this polarizer 20 is mounted with a specific base orientation in the polarizing unit 12. As more fully disclosed below, this base orientation will determine how other components are mounted in the ellipsometer. In FIG. 1, the base orientation is indicated by lines on the polarizer 20 which are taken to be substantially vertical. In any case, the light which passes through polarizer 20 continues along path 18 toward an electro-optical switch 22 which is also established on the path 18. This switch 22 is preferably of a type known in the pertinent art as a Pockels cell. For purposes of discussion herein, the terms electro-optical switch and Pockels cell will be used interchangeably.

Pockels cell 22 is mounted in polarizing unit 12 with its so-called fast axis oriented at an angle 24 relative to the base orientation of the polarizer 20. Specifically, the angle 24 is 45°. FIG. 1 also shows that polarizing unit 12 includes a pockels cell 26 with its so-called fast axis oriented at an angle 28 relative to the base orientation of the polarizer 20. The angle 28 is 22.5°. The importance of these specific relative orientations for the Pockels cells 22, 26 is based on the fact that in these orientations they are able to generate irradiation (polarization) states for the light beams emitted from ellipsometer 10 that are described by easily manageable Stokes vectors.

Figure 2:
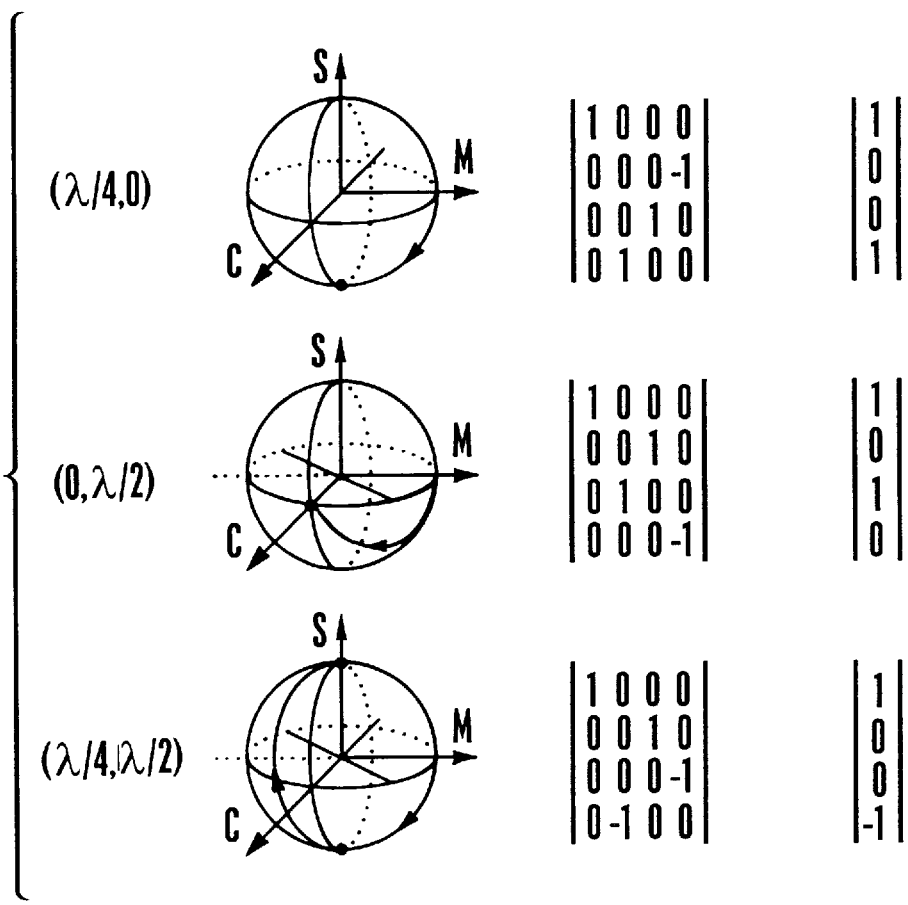
FIG. 2 is a visualization of Stokes vectors generated by the ellipsometer of the present invention.

As intended for the present invention, activation of the Pockels cells 22 and 26 will respectively cause phase shifts in the polarized light beam equal to $\lambda/4$ and $\lambda/2$. Consequently, in addition to an irradiation state (0,0) wherein the light is linearly polarized, by a concerted activation of the Pockels cells 22 and 26 the polarizing unit 12 can generate light having three other irradiation (polarization) states. These additional irradiation states are $(\lambda/4,0)$, $(0,\lambda/2)$ and $(\lambda/4,\lambda/2)$. In FIG. 2 the resultant rotations of the respective Stokes vectors and their respective Muller matrices are visualized for the $(\lambda/4,0)$, $(0,\lambda/2)$ and $(\lambda/4,\lambda/2)$ states of polarization. The result is four distinctive and independent states of polarization for the laser light which is emitted from the ellipsometer 10. As indicated in FIG. 1, this emitted light beam is focused and directed by a scanner 30 toward an eye 32.

Still referring to FIG. 1, the skilled artisan will appreciate that the light beam which is emitted from the polarizing unit 12 of ellipsometer 10 is reflected back along the path 18 until it is, in turn, reflected by the mirror 34. The light is thereby passed by the mirror 34 into the analyzing unit 14. In analyzing unit 14 the reflected light is further passed along a path 38 whereon it sequentially passes through a Pockels cell 40, a Pockels cell 42 and a polarizer 44. As indicated by the lines on polarizer 44 in FIG. 1, the polarizer 44 in analyzing unit 14 is oriented to be optically parallel to the polarizer 20 in polarizing unit 12. Further, the fast axis of Pockels cell 40 is oriented at an angle 46 relative to the polarizer 44, and the fast axis of Pockels cell 42 is oriented at an angle 48 relative to the polarizer 44. Angle 46 is 22.5° and angle 48 is 45°.

In a manner similar to that disclosed above for Pockels cells 22 and 26, and as intended for the present invention, activation of the Pockels cells 40 and 42 will respectively cause phase shifts in the polarized light on path 38 equal to $\lambda/4$ and $\lambda/2$. Consequently, analyzing unit 14 can establish four different and distinct detection states. Specifically, these include a detection state (0,0) wherein the Pockels cells 40 and 42 and passive, i.e. not activated, and the reflected light on path 38 is only linearly polarized by the polarizer 44. Additionally, by a concerted activation of the Pockels cells 40 and 42 the analyzing unit 14 can establish three other detection (polarization) states, namely $(\lambda/4,0)$, $(0,\lambda/2)$ and $(\lambda/4,\lambda/2)$.

After being subjected to a detection state in the analyzing unit 14, the reflected laser light beam is focused by a lens 50 and passed through a 100 $\mu$m pinhole 52 before being received by a detector 54. Preferably, the detector 54 is an avalanche photodiode detector of a type well known in the pertinent art.

FIG. 1 also shows that the ellipsometer 10 includes a processor 56 and a computer 58. For practical reasons the functions of both the processor 56 and computer 58 can be combined and controlled by a single unit. Regardless of how these components are physically connected, it is important to note that the processor 56 is electronically connected to the scanner 30, the Pockels cells 22 and 26 of polarizing unit 12, the laser diode 16, and the Pockels cells 40 and 42 of analyzing unit 14. Also, it is important to note that the computer 58 is connected to the detector 54. With these connections, the processor 56 can effectively control the operation of the ellipsometer 10 and the computer 58 can determine the information gained during operation of the ellipsometer.

OPERATION

In a general overview of its operation, the ellipsometer 10 of the present invention is first calibrated by determining the Müller matrix for the ellipsometer 10 itself ($M_{sc}$). The overall Müller matrix ($M_{all}$), which includes both the ellipsometer and the target tissue (e.g. cornea), is then measured. From these measurements the Müller matrix of the target tissue is determined in accordance with equation (2) set forth above. It happens that the measurements of both $M_{sc}$ and $M_{all}$ are accomplished using essentially the same procedure. The difference between these two procedures being the point where the ellipsometer 10 is actually focused. To determine $M_{sc}$, the ellipsometer 10 is focused on a mirror (not shown). To determine $M_{all}$, depending on the particular target tissue to be measured, the ellipsometer 10 is focused on preselected reflective surfaces in the eye 32.

Figure 3:
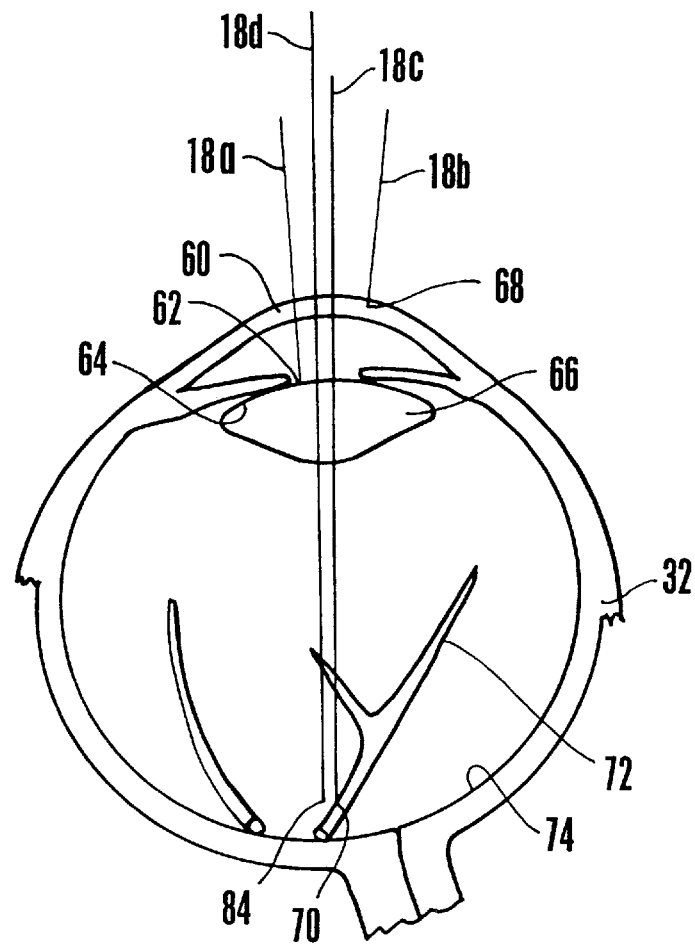
FIG. 3 is a cross-sectional view of an eye.

FIG. 3 shows the general anatomy of an eye 32 and several paths 18a–d which can be followed by laser beams emanating from ellipsometer 10 for the purpose of measuring the birefringent properties of the cornea 60. Specifically, beam path 18a indicates that the laser beam can pass through the cornea 60 of eye 32 and be focused at a focal point 62 located on the anterior surface 64 of lens 66. Also, the beam path 18b indicates that the laser beam can be focused at a focal point 68 inside the cornea 60 and, further, the beam path 18c indicates that the laser beam from ellipsometer 10 can be focused at a focal point 70 on a blood vessel 72 that is located on the surface of retina 74. In each instance, light passes along the particular path 18 and there is a specular reflection of this light back along the same path 18 after it has passed through, at least, a portion of the cornea 60. In accordance with the present invention, this reflected light is used to determine the birefringent properties of a particular portion of the cornea 60 through which the light passed.

Despite differences in these paths, the ellipsometer is operated in the same manner.

Once a focal point 62, 68 or 70 has been selected, the optical components of scanner 30 are set to focus the laser beam 18 onto the selected focal point. A polarization state is then established in the polarizing unit 12 for the laser beam that is to be passed along path 18 toward the eye 32. This is done by concertedly altering the voltage states of the pockels cells 22, 26 in polarizing unit 12. As indicated above, four specific polarization states can be independently generated. They are: (0,0), ($\lambda$/4,0), (0,$\lambda$/2) and ($\lambda$/4,$\lambda$/2). Simultaneously, by altering the voltage states of pockels cells 40, 42 in analyzing unit 14, four specific detection states can be independently established for ellipsometer 10. The detection states are: (0,0), ($\lambda$/4,0), (0,$\lambda$/2) and ($\lambda$/4,$\lambda$/2). Accordingly, sixteen different combinations of polarization states and detection states can be established.

To calculate the 16 coefficients of the Müller matrix that will define the birefringent properties of the target tissue, it is necessary to create 16 equations by taking 16 measurements for each single sampling point. In accordance with the above disclosure, the polarization unit 12 generates four linearly independent Stokesvectors $S_{in}$ by switching the voltages for the pockels cells 22, 26. These vectors pass the birefringent medium and the new polarization states are described by $S_{out}$. The analyzer unit 14 detects this light in four independent directions using the other pair of pockels cells 40, 42.

The calculation of $S_{out}$ is achieved by the multiplication of the Stokesvector with the matrices of the analyzer unit.

$$\underline{M}_{0,0}\vec{S}_{out} = \left( \frac{I+M}{2}, \frac{I+M}{2}, 0, 0 \right)$$

$$\underline{M}_{0,\lambda/4}\vec{S}_{out} = \left( \frac{I-S}{2}, \frac{I-S}{2}, 0, 0 \right)$$

$$\underline{M}_{\lambda/2,0}\vec{S}_{out} = \left( \frac{I+C}{2}, \frac{I+C}{2}, 0, 0 \right)$$

$$\underline{M}_{\lambda/2,\lambda/4}\vec{S}_{out} = \left( \frac{I+S}{2}, \frac{I+S}{2}, 0, 0 \right)$$

The analyzed Stokesvector is then:

$I = I_{0,\lambda/4} + I_{\lambda/2,\lambda/4}$ $M = 2I_{0,0} - I$ $C = 2I_{\lambda/2,0} - I$ $S = -I_{0,\lambda/4} + I_{\lambda/2,\lambda/4}$ with the indices specifying the voltage states of the pockels cells.

By way of example, in an application of the above procedure, the ellipsometer 10 is focused onto a blood vessel 72, and measurements are made along several different paths 18c through the cornea 60. In this way, the birefringent properties of various areas of the cornea 60 can be detected, examined, and compared with the other areas for inhomogeneities. When an area or region of birefringent inhomogeneity is detected, further analysis is possible. Specifically, a profile of the birefringent properties in the region can be obtained by taking a series of measurements in the region. This can be done in the cornea by using its anatomy to advantage.

Figure 4:
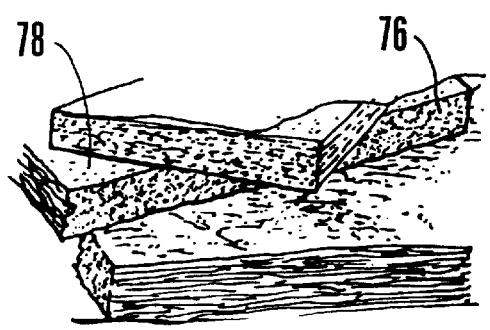
FIG. 4 is a representation of lamellae in the corneal stroma of the eye.

It is well known that the cornea 60 of any eye 32 is comprised of several different types of tissues. The most prevalent of these tissues is the stroma. Further, it is also well known that the stroma is comprised of many lamellae 76 which are layered in a manner shown schematically in FIG. 4. For purposes of the present invention, the ellipsometer 10 can be used to focus onto a focal point 68 which is located on the surface 78 of a lamella 76. The important factor here is that a specular reflection be obtained from the surface 78. As indicated, in FIG. 5, this can be done for several surfaces 78, of which the surfaces 78a, 78b and 78c are exemplary.

Once a region of birefringent inhomogeneity is found in the cornea 60, the ellipsometer 10 can be focused on successive lamella surfaces 78 in the region, and can be operated through the sixteen different modes at each of the surfaces 78. By this process, ellipsometer 10 is able to sequentially measure the birefringent properties of the cornea 60 in that particular region. More particularly, the distance "d" shown in FIG. 5 can be varied as desired to obtain as many as thirty two different birefringent measurements from as many surfaces 78 between the posterior surface 80 and the anterior surface 82 of the cornea 60.

Figure 5:
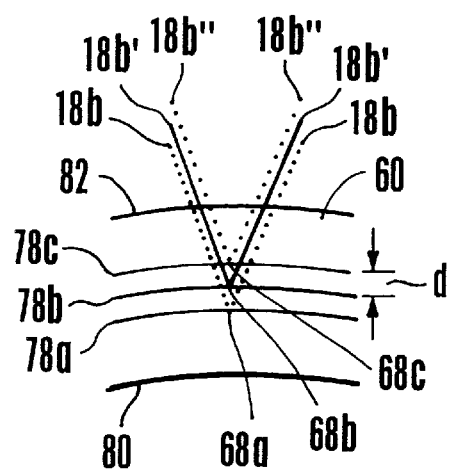
FIG. 5 is a representation of light beams focused onto stacked lamellae in the stroma.

As an example of the procedure just disclosed, consider that the ellipsometer 10 is focused along a path 18b to a focal point 68a. In FIG. 5 the boundaries of this path 18b are shown (exaggerated) as the beam is focused onto focal point 68a. For the present invention, it is to be appreciated that by employing a microscope objective with high numerical aperture the focal point 68a is a few microns in diameter and the field size which is covered by scanner 30 is an area on surface 78a which is approximately 250$\mu$m $\times$250$\mu$m. As so focused, the ellipsometer 10 is cycled through its sixteen different modes, and a measurement of the birefringent properties of the cornea 60 are obtained. Next, the ellipsometer 10 is focused along path 18b' onto focal point 68b of layer 78b and another birefringent measurement is obtained. The process is then repeated along path 18b" at focal point 68c on surface 78c, and is sequentially repeated thereafter until approximately thirty two different birefringent measurements have been obtained for tissue that is located along a line running substantially perpendicular to both the posterior surface 80 and anterior surface 82 of cornea 60. As will be appreciated by the skilled artisan, this procedure can be done again for as many other regions of birefringent inhomogeneity as are determined to be present in stroma 60. Further, as implied above, the regions of inhomogeneity can be determined by using reflections from either the anterior surface 64 of lens 66 or from a blood vessel 72 overlying the retina 74. In the later case the effects of lens 66 as the Müller matrix must be considered, but, in many instances this contribution will be negligible.

It will be appreciated that with similar procedures, the birefringent properties of the lens 66 can also be determined. For such a procedure it is preferable to use the beam path 18c and a focal point 70 on a blood vessel 72 overlying the retina 74.

Using ellipsometer 10 in essentially the same manner as described above, another procedure can be accomplished wherein the retina 74 is examined. Specifically, as shown in FIG. 3, the ellipsometer 10 can be directed along a path 18d and focused at a focal point 84 directly on the retina 74. A measurement from such a point, when compared with similar measurement taken from adjacent points on the retina 74 provide information on the birefringent properties of the deeper retinal layers, e.g. the neuronal retina. Using such measurements the thickness topography of the nerve fiber layer on the retina 74 can be estimated. This can be helpful as it is believed that atrophy of the nerve fiber layer is as early sign of glaucomateous disease.

While the particular ellipsometer as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for in-vivo measurement of optical characteristics of a birefringent material which comprises:

a polarizing unit for generating a beam of light having a preselected irradiation state;

an analyzing unit for receiving a reflection of said beam of light, said analyzing unit using a preselected detection state to determine a light intensity state of said beam;

electronic processor means for concertedly varying said polarization state of said polarizing unit with said detection state of said analyzing unit to determine a plurality of said intensity states for said beam; and computer means for using said plurality of intensity states to establish an optical characteristic for the material.

2. A system as recited in claim 1 wherein said light beam is directed along a path and said polarizing unit comprises:

a light source for generating said light beam;

a first polarizer mounted on said path for passing plane-polarized light from said light source along said path;

a first electro-optical cell for selectively changing said polarization state of said plane-polarized light by creating a first phase shift; and a second electro-optical cell for selectively changing said polarization state of said plane-polarized light by creating a second phase shift.

3. A system as recited in claim 2 wherein said light source is a diode laser operating at a wavelength of 670 nm.

4. A system as recited in claim 2 wherein said light source is a diode laser operating at a wavelength of 785 nm.

5. A system as recited in claim 2 wherein said analyzing unit comprises:

a first electro-optical cell for selectively changing said polarization state of said reflected light by creating a first phase shift;

a second electro-optical cell for selectively changing said polarization state of said reflected light by creating a second phase shift;

a second polarizer mounted on said path for passing said reflected light from said second electro-optical cell along said path;

and a detector for receiving said light from said second polarizer to detect said light intensity state of said light beam.

6. A system as recited in claim 5 wherein said detector is an avalanche photo-diode.

7. A system as recited in claim 5 wherein said first electro-optical cell of said polarizing unit can phase shift said light 0° or $\lambda/4$, wherein said second electro-optical cell of said polarizing unit can phase shift said light 0° or $\lambda/2$, wherein said first electro-optical cell of said analyzing unit can phase shift said light 0° or $\lambda/4$, and wherein said second electro-optical cell of said analyzing unit can phase shift said light 0° or $\lambda/2$.

8. A system as recited in claim 7 wherein said first electro-optical cell of said polarizing unit is oriented at 450 relative to said first polarizer, said second electro-optical cell of said polarizing unit is oriented at 22.5° relative to said first polarizer, said first electro-optical cell of said analyzing unit is oriented at 450 relative to said second polarizer, and said second electro-optical cell of said analyzing unit is oriented at 22.520 0 relative to said second polarizer.

9. A system as recited in claim 7 wherein said first polarizer is oriented substantially parallel to said second polarizer.

10. A system as recited in claim 7 wherein said first and second electro-optical cells of said polarizing unit, and said first and second electro-optical cells of said analyzing unit are connected to said electronic processor means to determine said intensity states for sixteen linearly independent states of polarization.

11. A system as recited in claim 10 further comprising computer means for combining said sixteen linearly independent states of polarization to obtain a measurement of a birefringent characteristic of the cornea.

12. A system as recited in claim 10 further comprising means for selectively focusing said beam of light.

13. A system as recited in claim 12 wherein said material is the cornea of the eye and said system is focused on a surface of the lens of the eye to determine optical characteristics for a region of the cornea.

14. A system as recited in claim 12 wherein said material is the cornea of the eye and said system is focused on blood vessels overlying the retina to obtain optical characteristics for a region of the cornea.

15. A system as recited in claim 12 wherein said material is the cornea of the eye and said system is focused on a plurality of layers of the cornea.

16. A system as recited in claim 12 wherein said material is the retina of the eye and said system is focused onto the retina.

17. A method for in-vivo measurement of optical characteristics of a cornea which comprises the steps of:

generating a beam of light having a preselected polarization state;

receiving a reflection of said beam of light, an analyzing unit using a preselected detection state to determine a light intensity state of said beam;

concertedly varying said polarization state of said polarizing unit with said detection state of said analyzing unit to determine a plurality of said intensity states for said beam; and using said plurality of intensity states to establish an optical characteristic for the cornea.

18. A method as recited in claim 17 wherein said generating step is accomplished by creating a phase shift in said beam of light for a respective polarization state of (0,0), ($\lambda/4$,0). (0.$\lambda/2$) and ($\lambda/4,\lambda/2$) and said receiving step is accomplished by creating a phase shift in said beam of light for a respective detection state of (0,0), ($\lambda/4$,0). (0.$\lambda/2$) and ($\lambda/4,\lambda/2$.

19. A method as recited in claim 17 which further includes the steps of:

selectively focusing said light beam through a first portion of the material to establish said optical characteristic;

refocusing said light beam through another portion of the material to establish another said optical characteristic;

repeating said refocusing step, as necessary; and comparing said optical characteristics, to identify a region of inhomogeneous elastic properties of the material.

20. A method as recited in claim 19 wherein the material is the cornea of the eye and said focusing and refocusing steps are accomplished by focusing the light beam on a surface of the lens of the eye.

21. A method as recited in claim 19 wherein the material is the cornea of the eye and said focusing and refocusing steps are accomplished by focusing the light beam on blood vessels overlying the retina of the eye.

22. A method as recited in claim 19 wherein the material is the cornea of the eye and said focusing and refocusing steps are accomplished through the cornea of the eye in said region of inhomogeneous elastic properties.

23. A method as recited in claim 22 wherein said focusing and refocusing steps are accomplished on a plurality of layers of the cornea.

* * * * *

UNITED STATES PATENT AND TRADEMARK OFFICE
CERTIFICATE OF CORRECTION

PATENT NO. : 5,822,035
DATED : October 13, 1998
INVENTOR(S) : Josef F. Bille

It is certified that error appears in the above-identified patent and that said Letters Patent is hereby corrected as shown below:

Column 9, Line 67
DELETE
[electro-optical cell of said polarizing unit is oriented at 450]
INSERT
--electro-optical cell of said polarizing unit is oriented at 45°--

Column 10, Line 4
DELETE
[unit is oriented at 450 relative to said second polarizer]
INSERT
--unit is oriented at 45° relative to said second polarizer--

Column 10, Line 6
DELETE
[oriented at 22.520 0 relative to said second polarizer]
INSERT
--oriented at 22.5° relative to said second polarizer--

Signed and Sealed this

Nineteenth Day of January, 1999

Attest:

Attesting Officer

*Acting Commissioner of Patents and Trademarks*